US005131047A

United States Patent [19]

Hashimoto et al.

[11] Patent Number: 5,131,047

[45] Date of Patent: Jul. 14, 1992

[54] NOISE SUPPRESSOR

[75] Inventors: Hiroyuki Hashimoto, Daito; Nakama Yasutoshi, Ikoma; Tomokazu Suzuki; Terai Kenichi, both of Osaka; Suzuki Ryoji, Nara, all of Japan

[73] Assignee: Matsushita Electric Industrial Co., Ltd., Osaka, Japan

[21] Appl. No.: 712,038

[22] Filed: Jun. 7, 1991

[30] Foreign Application Priority Data

Jun. 11, 1990 [JP] Japan ................................ 2-151949

[51] Int. Cl.[5] ......................... H04R 5/00; H04R 3/02; A61F 2/20; H04B 15/00

[52] U.S. Cl. ........................................ 381/71; 381/13; 381/73.1; 381/93; 381/94

[58] Field of Search .................... 381/13, 86, 71, 73.1, 381/93, 94

[56] References Cited

U.S. PATENT DOCUMENTS 4,683,590 7/1987 Miyoshi et al. ....................... 381/71
4,736,431 4/1988 Allie et al. ........................... 381/71
4,987,598 1/1991 Eriksson ............................... 381/71
5,018,202 5/1991 Takahashi et al. .................... 381/71

FOREIGN PATENT DOCUMENTS

WO90/09655 8/1990 PCT Int'l Appl. .

*Primary Examiner*—Forester W. Isen
*Assistant Examiner*—Jack Chiang
*Attorney, Agent, or Firm*—Wenderoth, Lind & Ponack

[57] ABSTRACT

A noise suppressor is disclosed in which a noise signal is detected by a first detector, then processed by an adaptive filter, and an output signal from the adaptive filter and an audio signal from audio equipment are added by an adder and reproduced by a speaker. The sound signal thus reproduced by the speaker and the noise signal are detected by a second detector located at a listening point and sent to a filter control circuit. The filter control circuit possesses the signal sent from the second detector and the audio signal from the audio equipment having a transfer function from the adder to the filter control circuit convoluted thereby to remove the audio signal component therefrom. The adaptive filter adaptively controls the noise signal in response to the output signal from the filter control circuit.

6 Claims, 4 Drawing Sheets

NOISE SUPPRESSOR

BACKGROUND OF THE INVENTION

1. Field of the Invention

This invention relates to a noise suppressor using an active noise control under a noisy environmental condition.

2. Description of the Prior Art

Recently, the active noise control method has been proposed in which an environmental noise is subjected to noise suppression at the listening point thereof by outputting a control sound signal from a speaker using the digital signal technology.

A noise suppressor according to the prior art will be described below while referring to the drawings attached.

FIG. 4 is a block diagram of a noise suppressor of the prior art. In FIG. 4, 1*a* and 1*b* are microphones, 2 is an adaptive filter, 4 a speaker, and 8 a noise source. With the noise suppressor arranged as above, the operation thereof will be explained.

A noise signal detected by the microphone 1*a* is inputted to the adaptive filter 2 for adaptive control. The signal thus adaptively controlled is reproduced by the speaker 4. The sound signal thus reproduced is interfered with a noise signal outputted from the noise source 8 to generate an interference sound signal. The interference sound signal thus generated is detected by the microphone 1*b*. The signal thus detected is sent to the adaptive filter 2 as a control signal by an algorism such as, for example, the LMS method. The adaptive filter 2 performs the adaptive control so as to make the control signal small so that the noise signal at a position where the microphone 1*b* is located can be canceled with the sound signal reproduced by the speaker 4, resulting in a reduction in noise.

FIG. 5 is a block diagram of a noise suppressor according to the prior art, which is typically applied in a space where an audio signal is to be reproduced. In FIG. 5, 1*a* and 1*b* are microphones, 2 is an adaptive filter, 4*a* and 4*b* are speakers, 5 is audio equipment and 8 is a noise source.

This noise suppressor has the same operation as that shown in FIG. 4. In this case, however, a sound signal detected by the microphone 1*b* contains a noise signal from the noise source 8 and a canceling signal from the speaker 4 as well as additionally contains an audio signal from the speaker 4*b*. As a result, by being subjected to the influence of the audio signal which is independent of the noise signal to be inputted, a coefficient of the adaptive filter 2 cannot be convergently determined or can be varied, resulting in an unstable operation of adaptive control. As a result, in some cases, the noise may not be sufficiently attenuated or additionally increased on the contrary.

FIG. 6 is a block diagram of a noise suppressor which has an adder to be used in combination with a speaker additionally to that shown in FIG. 5. In FIG. 6, 1*a* and 1*b* are microphones, 2 an adaptive filter, 3 an adder, 4 a speaker, 5 an audio device and 8 a noise source.

Even in this case, the adaptive filter 2 cannot provide a stable adaptive control due to the influence of an audio signal from the audio device 5 as pointed out in FIG. 5, resulting in occurring such a case that the noise is insufficiently attenuated or additionally increased.

As explained above, with the noise suppressor according to the prior art, such a problem has been pointed out that when an audio signal is to be reproduced in a noisy environment, insufficient attenuation or unstable operation of adaptive control of a noise results.

SUMMARY OF THE INVENTION

An object of this invention is to provide a noise suppressor in which when an audio signal is to be reproduced in a noisy environment, a signal-to-noise (S/N) ratio is improved by attenuating a noise signal sufficiently and stably.

In order to attain the above-mentioned object, a noise suppressor of this invention comprises a first detector for detecting a noise or a vibration of a noise source, an adaptive filter for processing the noise signal thus detected, an adder for adding an output signal from the adaptive filter and an audio signal from audio equipment, a speaker for reproducing an output signal from the adder, a second detector for detecting a sound signal at a listening point, a digital filter for processing an audio signal from the audio equipment, and a filter control circuit for computing a signal detected by the second detector and an output signal from the digital filter for controlling the adaptive filter and the digital filter.

With the arrangement as shown above, a noise suppressor of this invention makes possible that the filter control circuit computes an output signal from the second detector and an output signal from the digital filter to remove the audio signal component so that the adaptive filter can perform the adaptive control with the noise signal component only, which means that even when an audio signal is to be reproduced, attenuation of a noise signal can be made sufficiently and stably.

Another noise suppressor of this invention in order to attain the above-mentioned object comprises a first detector for detecting a noise or a vibration of a noise source, a first digital filter for processing the noise signal thus detected, an adder for adding an output signal from the first digital filter and an audio signal from audio equipment, a speaker for reproducing an output signal from the adder, a second detector for detecting a sound signal at a listening point, a second digital filter for processing an audio signal from the audio equipment, a computing circuit for computing an audio signal from the audio equipment and an output signal from the second digital filter, a first switching circuit for effecting switching of an output signal from the first detector and audio signal from the audio equipment, a coefficient control circuit for controlling a coefficient of the first digital filter and that of the second digital filter in response to an output signal from the first switching circuit and an output signal from the computing circuit, and a second switching circuit for switching an output signal from the coefficient control circuit to the first digital filter or to the second digital filter.

With the arrangement as shown above, another noise suppressor of this invention makes possible that the computing circuit computes an output signal from the second detector and that from the second digital filter to remove the audio signal component so that the coefficient control circuit can control a coefficient of the first digital filter with the noise signal component only, which means that even when an audio signal is to be reproduced, attenuation of a noise signal can be made sufficiently and stably.

PREFERRED EMBODIMENTS OF THE INVENTION

A noise suppressor according to a first embodiment of this invention will be described below while referring the drawings.

Figure 1:
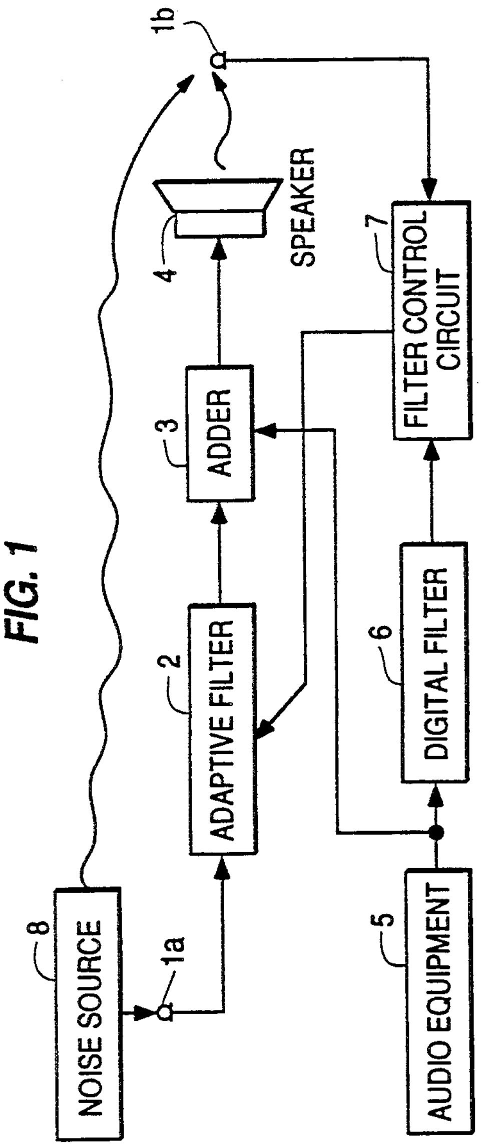
FIG. 1 is a block diagram of a noise suppressor showing an example of, a first embodiment of this invention.

FIG. 1 is a block diagram of a noise suppressor showing an example of the first embodiment of this invention. In FIG. 1, 1*a* and 1*b* are microphones, 2 is an adaptive filter, 3 an adder, 4 a speaker, 5 audio equipment such as a radio, an audio tape player or an audio disc player, 6 a digital filter, 7 a filter control circuit and 8 a noise source.

With the arrangement as shown above, the operation of the noise suppressor will be explained. A noise signal detected by the microphone 1*a* is first sent to the adaptive filter 2 for processing and inputted to the adder 3. On the other hand, an audio signal from the audio equipment 5 is inputted to the adder 3. The noise signal and the audio signal are added by the adder 3 and sent to the speaker 4 for reproduction. The microphone 1*b* detects the sound signal thus reproduced by the speaker 4 and a noise signal from the noise source 8 and inputs them to the filter control circuit 7. On the other hand, the audio signal from the audio equipment 5 is also inputted to the digital filter 6. The digital filter 6 approximates a transfer function from the adder 3 to the microphone 1*b*. As a result, the audio signal convolutes the transfer function and outputted to the filter control circuit 7. The filter control circuit 7 subtracts an output signal of the digital filter 6 from an output signal from the microphone 1*b* and the signal thus obtained is made as a control signal for the adaptive filter 2. This control signal has the audio signal component removed, so that the adaptive filter 2 performs the adaptive control with the noise signal component only. As a result, by minimizing the control signal, the noise signal can be attenuated at a listening point where the microphone 1*b* is located.

As explained above, the noise suppressor of this embodiment makes possible that the filter control circuit 7 subtracts an output signal of the digital filter 6 approximating a transfer function from the adder 3 to the microphone 1*b* from a detected signal by the microphone 1*b* to generate a control signal for the adaptive filter 2, which does not contain the audio signal component, and the adaptive filter 2 performs the adaptive control with the control signal containing the noise signal component only, so that the noise signal can be attenuated sufficiently and stably.

Next, another example of the first embodiment will be described below by referring to the drawing.

Figure 2:
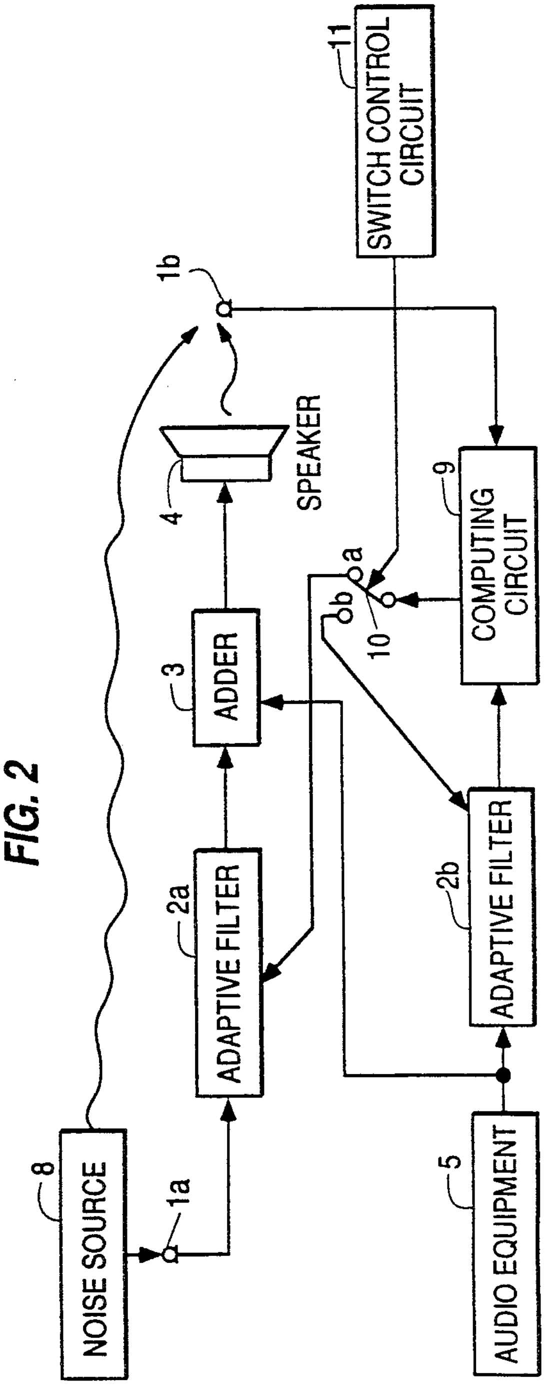
FIG. 2 is a block diagram of a noise suppressor showing another example, of the first embodiment of this invention.

FIG. 2 is a block diagram of a noise suppressor showing another example of this embodiment. In FIG. 2, 1*a* and 1*b* are microphones, 2*a* and 2*b* adaptive filters, 3 an adder, 4 a speaker, 5 audio equipment, 8 a noise source 9 a computing circuit, 10 a switch and 11 a switch control circuit.

With the arrangement as shown above, the operation of this noise suppressor will be explained below. For the sake of simplification, the explanation will be made on the case when an engine noise within a car room is to be canceled. This means that the noise source 8 is an engine. First, the switch control circuit 11 is controlled so that the switch 10 is switched to the b-side while being the engine 8 OFF, and the audio equipment 5 is acted on. An audio signal outputted from the audio equipment 5 is sent through the adder 3 to the speaker 4 for reproduction. The signal thus reproduced by the speaker 4 is converted by the microphone 1*b* into an electric signal to be sent to the computing circuit 9. On the other hand, the audio signal from the audio equipment 5 is inputted to the adaptive filter 2*b*, and the output signal from the adaptive filter 2*b* is sent to the computing circuit 9. The computing circuit 9 computes the detected signal by the microphone 1*b* and the output signal from the adaptive filter 2*b* and the signal thus obtained is sent to the adaptive filter 2*b* as a control signal for adaptive control. In this case, the adaptive filter 2*b* adaptively controls so that the control signal thus sent from the computing circuit 9 is attenuated.

Next, the audio equipment 5 is ceased to operate, the switch control circuit 11 is controlled so that the switch 10 is switched to the a-side, and the engine 8 is turned ON. Then, the microphone 1*a* detects an engine noise generated from the engine 8. The noise signal thus detected is processed by the adaptive filter 2*a*, and inputted via the adder 3 to the speaker 4 for reproduction. On the other hand, the engine noise generated from the engine 8 is detected by the microphone 1*b* located at the listening point. At the same time, it detects the reproduced sound signal from the speaker 4. The signal thus detected is provided via the computing circuit 9 to the adaptive filter 2*a* as a control signal thereof. The adaptive filter 2*a* performs the adaptive control so that the control signal thus provided is attenuated. As a result, the engine noise at the listening point can be canceled with the sound signal reproduced by the speaker 4.

At the time point when the above-mentioned control is completed, the audio equipment 5 is acted on. Then, the audio signal from the audio equipment 5 and the output signal from the adaptive filter 2*a* are added by the adder 3 and sent to the speaker 4 for reproduction. The sound signal thus reproduced by the speaker 4 and the engine noise from the engine 8 are detected by the microphone 1*b* and sent to the computing circuit 9. On the other hand, the audio signal of the audio equipment 5 is subjected to signal processing by the adaptive filter 2*b* and sent to the computing circuit 9. Accordingly, as explained above, by effecting the adaptive filter 2*b* and the computing circuit 9, the output signal from the computing circuit 9 does not contain the audio signal component, so that the adaptive filter 2 performs the adaptive control with the engine noise component only. As a result, even when an audio signal is to be reproduced, the adaptive filter 2*a* operates in the same manner as in case that it is not to be reproduced.

As explained above, the noise suppressor showing another example of the first embodiment makes possible that an output signal from the computing circuit 9 is controlled so as not to contain the audio signal component by effecting the adaptive filter 2*b* and the computing circuit 9 and the adaptive filter 2*a* performs the adaptive control with the engine noise component only, thus being capable of providing a sufficient and stable attenuation of a noise.

In addition, it is clear from the above-mentioned explanation that if the identification of the adaptive filter 2*b* is completed, the identification of the adaptive filter 2*a* may be carried out while the audio equipment 5 is in operation. Further in addition, the noise to be canceled is not limited to those generated from a car vehicle, any one by various noise sources may be targeted.

Next, a noise suppressor showing an example of a second embodiment of this invention will be described below while referring to the drawing.

Figure 3:
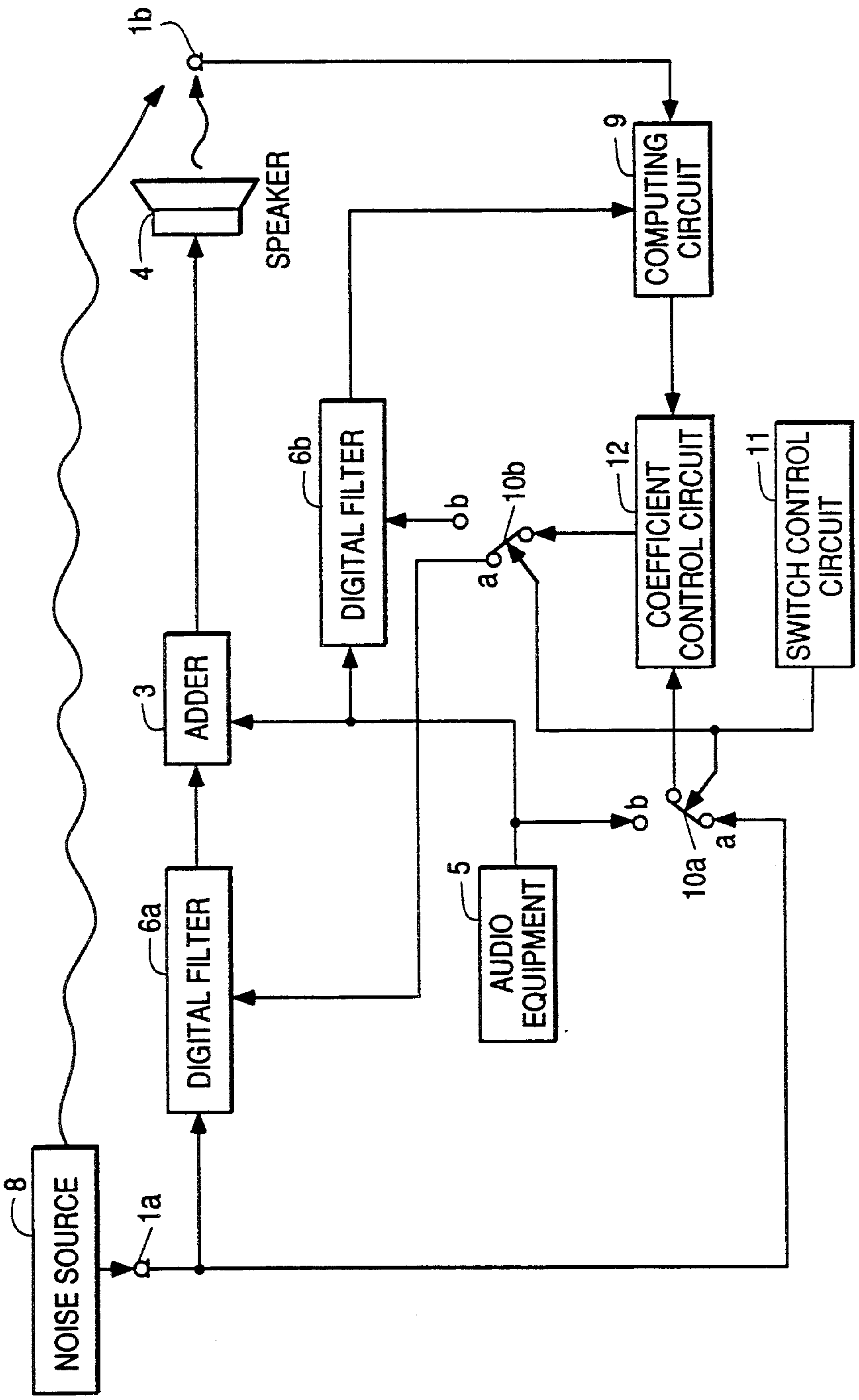
FIG. 3 is a block diagram of a noise suppressor showing an example of a second embodiment of this invention.
Figure 4:
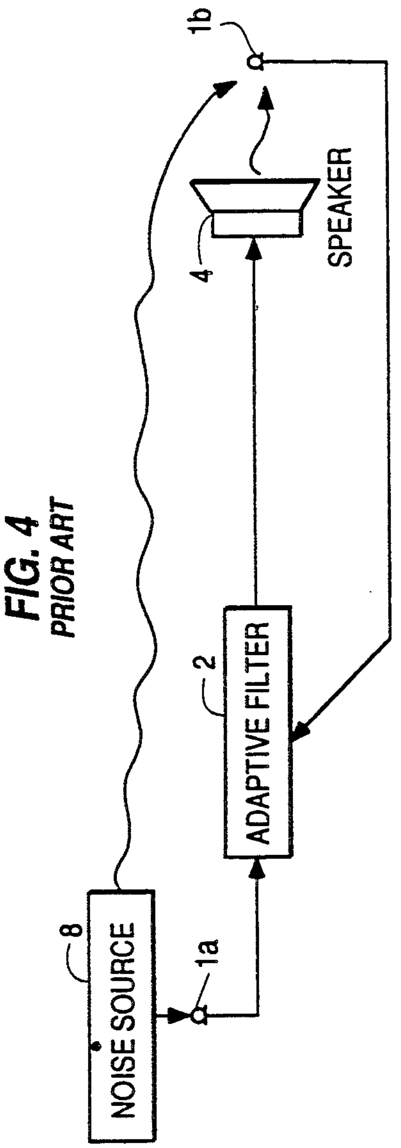
FIG. 4 PRIOR ART
FIG. 4 is a block diagram of a noise suppressor of the prior art.
Figure 5:
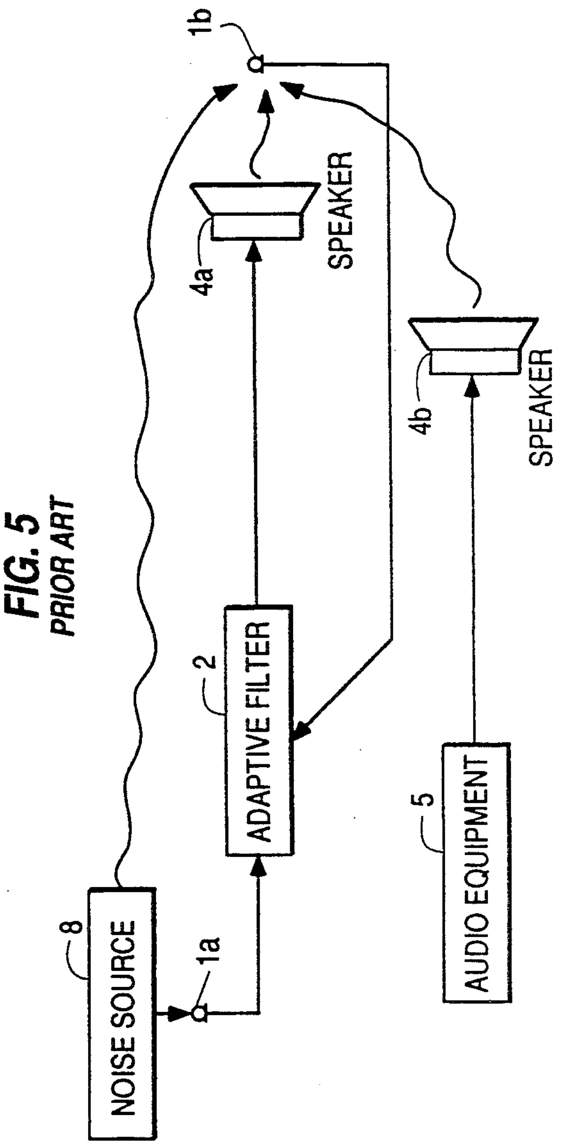
FIG. 5 PRIOR ART
FIGS. 5 and 6 each is a block diagram of a noise suppressor of the prior art, in which an audio signal is to be reproduced.
Figure 6:
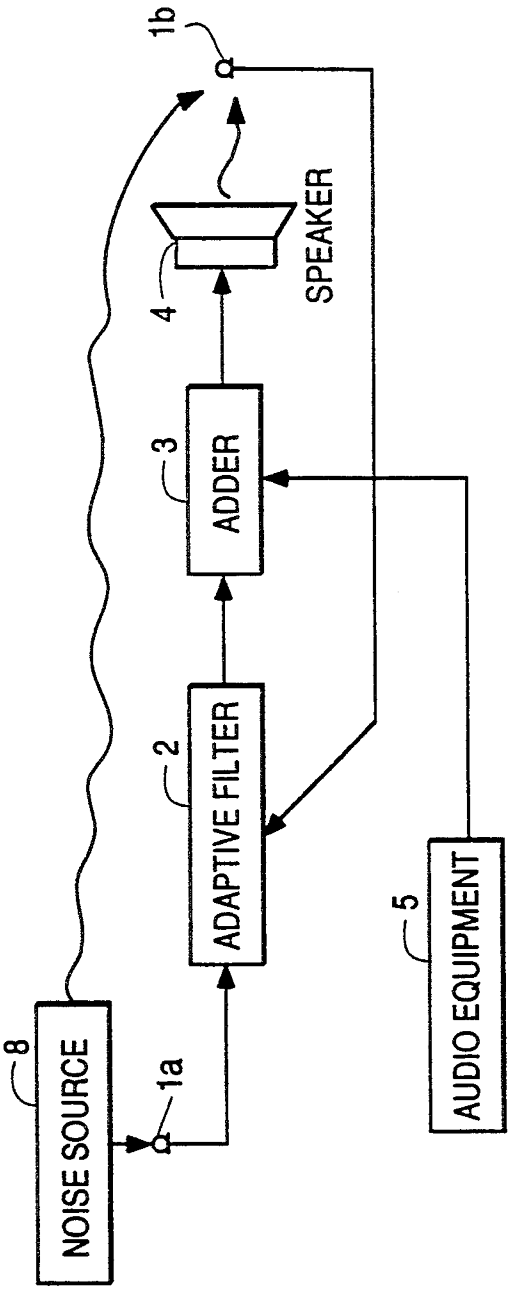
FIG. 6 PRIOR ART

FIG. 3 is a block diagram of a noise suppressor showing an example of the second embodiment. In FIG. 3, 1*a* and 1*b* are microphones, 3 an adder, 4 a speaker, 5 audio equipment, 6*a* and 6*b* digital filter, 8 a noise source, 9 a computing circuit, 10*a* and 10*b* switches, 11 a switch control circuit and 12 a coefficient control circuit.

With the arrangement as shown above, the operation will be explained below. For the sake of simplification, the explanation will be made on the case when an engine noise within a car room is to be canceled. That is, the noise source 8 is an engine. First, the switch control circuit 11 is controlled so that the switches 10*a* and 10*b* are switched to the respective b-sides while being the engine 8 OFF, and the audio equipment 5 is operated. An audio signal outputted from the audio equipment 5 is sent through the adder 3 to the speaker 4 for reproduction. The signal thus reproduced by the speaker 4 is converted by the microphone 1*b* into an electric signal to be sent to the computing circuit 9. On the other hand, the audio signal from the audio equipment 5 is inputted to the digital filter 6*b*, and the output signal from the adaptive filter 6*b* is sent to the computing circuit 9. The computing circuit 9 computes the electric signal sent from the microphone 1*b* and the output signal from the digital filter 6*b* and the signal thus obtained is sent to the coefficient control circuit 12. The coefficient control circuit 12 processes the output signal from the computing circuit 9 and the audio signal from the audio equipment 5 to obtain a coefficient of the digital filter 6*b*. In this case, the coefficient control circuit 12 operates so that the signal sent from the computing circuit 9 is minimized. So operating that the audio signal component of the output signal from the computing circuit 9 is attenuated.

Next, the switch control circuit 11 is controlled so that the switches 10*a* and 10*b* are switched to the respective a-sides and the engine 8 is turned ON. Then, the microphone 1*a* detects an engine noise generated from the engine 8. The engine noise thus detected is processed by the digital filter 6*a* and sent to the adder 3. In the adder 3, the audio signal from the audio equipment 5 and the output signal from the digital filter 6*a* are added to each other and sent to the speaker 4 for reproduction. The reproduced signal by the speaker 4 and the engine noise from the engine 8 are detected by the microphone 1*b* to be sent to the computing circuit 9. On the other hand, the audio signal from the audio equipment 5 is subjected to signal processing by the digital filter 6*b* to be sent to the computing circuit 9. Then, as explained above, by effecting the digital filter 6*b* and the computing circuit 9, the output signal from the operation circuit 9 does not contain the audio signal component, and the coefficient control circuit 12 operates so as to minimize the engine noise component of the output signal from the computing circuit 9. Thus, the coefficient of the digital filter 6*a* is obtained to attenuate the engine noise.

As described above, according to this embodiment, by effecting the digital filter 6*b*, the computing circuit 9 and the coefficient control circuit 12, an output signal from the computing circuit 9 is controlled so as not to contain the audio signal component, and the digital filter 6*a* and the coefficient control circuit 12 perform the adaptive control with the engine noise component only, thus being capable of attenuating the engine noise sufficiently and stably.

In addition, the noise to be canceled is not limited to those generated from a car vehicle, any one of various noise sources may be targeted as a noise source.

What is claimed is:

1. A noise suppressor comprising: a first detector for detecting a noise or a vibration of a noise source;
   - an adaptive filter for processing a noise signal detected by said first detector;
   - an adder for adding an output signal from said adaptive filter and an audio signal outputted from audio equipment;
   - a speaker for reproducing an output signal from said adder;
   - a second detector for detecting a sound signal at a listening point;
   - a digital filter for processing an audio signal outputted from said audio equipment; and
   - a filter control circuit for processing a signal detected by said second detector and an output signal from said digital filter for controlling said adaptive filter and said digital filter.

2. A noise suppressor as claimed in claim 1, wherein said digital filter approximates a transfer function from said adder to said filter control circuit.

3. A noise suppressor as claimed in claim 1, wherein said digital filter is another adaptive filter.

4. A noise suppressor as claimed in claim 3, wherein said filter control circuit comprises:
   - a computing circuit for computing a signal detected by said second detector and an output signal from said another adaptive filter; and
   - a switching circuit for selecting a signal thus obtained by said computing circuit to output to either said adaptive filter or said another adaptive filter.

5. A noise suppressor comprising:
   - a first detector for detecting a noise or a vibration of a noise source;
   - a first digital filter for processing a noise signal detected by said first detector;
   - an adder for adding an output signal from said first digital filter and an audio signal from audio equipment;
   - a speaker for reproducing an output signal from said adder;
   - a second detector for detecting a sound signal at a listening point;
   - a second digital filter for processing an audio signal outputted from said audio equipment;
   - a computing circuit for computing a signal detected by said second detector and an output signal from said second digital filter;

a first switching circuit for effecting switching of an output signal from said first detector and an audio signal from said audio equipment;

a coefficient control circuit for controlling a coefficient of said first digital filter and that of second digital filter in response to an output signal from said first switch circuit and that from said computing circuit; and a second switching circuit for switching an output signal from said coefficient control circuit to said first and second digital filters.

6. A noise suppressor as claimed in claim 5, wherein when said first switching circuit is switched as to receive an audio signal from said audio equipment and said second switching circuit is switched to said second digital filter, a coefficient of said second digital filter is controlled by said coefficient control circuit, and when said first switching circuit is switched as to receive an output signal from said first detector and said second switching circuit is switched to said first digital filter, a coefficient of said first digital filter is controlled by said coefficient control circuit, thereby effecting a noise suppression.

* * * * *